US012605041B2

(12) United States Patent
Oosake

(10) Patent No.: US 12,605,041 B2
(45) Date of Patent: Apr. 21, 2026

(54) MEDICAL IMAGE PROCESSING APPARATUS, ENDOSCOPE SYSTEM, AND METHOD FOR OPERATING MEDICAL IMAGE PROCESSING APPARATUS FOR RECOGNIZING A REGION OF INTEREST IN MEDICAL IMAGE

(71) Applicant: FUJIFILM Corporation, Tokyo (JP)

(72) Inventor: Masaaki Oosake, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 880 days.

(21) Appl. No.: 17/177,216

(22) Filed: Feb. 17, 2021

(65) Prior Publication Data

US 2021/0169306 A1     Jun. 10, 2021

Related U.S. Application Data

(63) Continuation of application No. PCT/JP2019/032168, filed on Aug. 16, 2019.

(30) Foreign Application Priority Data

Aug. 23, 2018    (JP) ................................. 2018-156407

(51) Int. Cl.
*A61B 1/00*          (2006.01)
*A61B 1/06*          (2006.01)

(52) U.S. Cl.
CPC .... *A61B 1/00045* (2013.01); *A61B 1/000094* (2022.02); *A61B 1/00042* (2022.02); *A61B 1/0655* (2022.02); *A61B 1/0661* (2013.01)

(58) Field of Classification Search
None
See application file for complete search history.

(56) References Cited

U.S. PATENT DOCUMENTS

| | | | |
|---|---|---|---|
| 7,783,094 B2 | 8/2010 | Collins et al. | |
| 2008/0039692 A1* | 2/2008 | Hirakawa | .......... A61B 1/00045 600/160 |
| 2008/0151187 A1* | 6/2008 | Tsukada | ............. G01N 21/4795 351/206 |

(Continued)

FOREIGN PATENT DOCUMENTS

| | | |
|---|---|---|
| CN | 106102556 | 11/2016 |
| CN | 106659362 | 5/2017 |

(Continued)

OTHER PUBLICATIONS

"Office Action of Japan Counterpart Application" with English translation thereof, issued on Apr. 26, 2022, p. 1-p. 6.

(Continued)

*Primary Examiner* — John P Leubecker
(74) *Attorney, Agent, or Firm* — JCIPRNET

(57) ABSTRACT

A processor device includes an image signal acquiring unit, an image processing unit, and a display control unit. The image signal acquiring unit acquires a digital image signal corresponding to an observation mode from an endoscope. The image processing unit includes a region-of-interest-mode image processing unit. The display control unit performs switching control of switching between a first display method in which an endoscopic image is displayed in real time and a second display method in which a recognition result list is displayed.

17 Claims, 8 Drawing Sheets

(56)                References Cited

U.S. PATENT DOCUMENTS

| | | | |
|---|---|---|---|
| 2012/0302847 A1* | 11/2012 | Ozawa | A61B 1/063 |
| | | | 600/339 |
| 2013/0152020 A1* | 6/2013 | Nishiyama | G16H 30/20 |
| | | | 715/835 |
| 2015/0272422 A1* | 10/2015 | Aoyama | A61B 1/0661 |
| | | | 348/68 |
| 2015/0272429 A1 | 10/2015 | Shigeta | |
| 2016/0374602 A1* | 12/2016 | Koshiba | A61B 1/063 |
| | | | 600/327 |
| 2017/0014021 A1* | 1/2017 | Kuramoto | A61B 1/043 |
| 2017/0112356 A1* | 4/2017 | Mitsui | H04N 23/80 |
| 2017/0251932 A1* | 9/2017 | Kaku | A61B 5/1071 |
| 2018/0153384 A1 | 6/2018 | Ikemoto et al. | |
| 2018/0214005 A1* | 8/2018 | Ebata | A61B 5/02007 |
| 2018/0242817 A1* | 8/2018 | Imaizumi | G06T 11/60 |
| 2019/0114738 A1* | 4/2019 | Sonoda | A61B 1/000094 |
| 2019/0374088 A1* | 12/2019 | Watanabe | A61B 1/0638 |
| 2019/0380617 A1* | 12/2019 | Oosake | A61B 1/00006 |
| 2020/0022560 A1* | 1/2020 | Oosake | A61B 1/0684 |
| 2020/0129042 A1* | 4/2020 | Takahashi | H04N 7/18 |
| 2020/0143936 A1* | 5/2020 | Kamon | G16H 30/40 |
| 2021/0100426 A1* | 4/2021 | Ariyoshi | A61B 1/05 |

FOREIGN PATENT DOCUMENTS

| | | |
|---|---|---|
| CN | 108135457 | 6/2018 |
| CN | 110475503 | 11/2019 |
| EP | 3263011 | 1/2018 |
| EP | 3603481 | 2/2020 |
| JP | 2008541889 | 11/2008 |
| JP | 2009061174 | 3/2009 |
| JP | 2009066301 | 4/2009 |
| JP | 2012249936 | 12/2012 |
| JP | 2016019569 | 2/2016 |
| JP | 2016158828 | 9/2016 |
| WO | 2016136700 | 9/2016 |
| WO | 2017073337 | 5/2017 |

OTHER PUBLICATIONS

"Office Action of Japan Counterpart Application" with English translation thereof, issued on Dec. 14, 2021, p. 1-p. 8.

Office Action of China Counterpart Application, with English translation thereof, issued on Oct. 19, 2023, pp. 1-18.

"Search Report of Europe Counterpart Application", issued on Sep. 9, 2021, p. 1-p. 8.

"International Search Report (Form PCT/ISA/210) of PCT/JP2019/032168," mailed on Nov. 5, 2019, with English translation thereof, pp. 1-3.

"Written Opinion of the International Searching Authority (Form PCT/ISA/237) of PCT/JP2019/032168," mailed on Nov. 5, 2019, with English translation thereof, pp. 1-10.

"Office Action of Europe Counterpart Application", issued on Mar. 4, 2024, pp. 1-4.

"Office Action of China Counterpart Application", issued on Mar. 9, 2024, with English translation thereof, pp. 1-24.

* cited by examiner

Recognition results

Real-time display

1

There is a lesion portion

2

There is a lesion portion

MEDICAL IMAGE PROCESSING APPARATUS, ENDOSCOPE SYSTEM, AND METHOD FOR OPERATING MEDICAL IMAGE PROCESSING APPARATUS FOR RECOGNIZING A REGION OF INTEREST IN MEDICAL IMAGE

CROSS-REFERENCE TO RELATED APPLICATIONS

This application is a Continuation of PCT International Application No. PCT/JP2019/032168 filed on 16 Aug. 2019, which claims priority under 35 U.S.C § 119(a) to Japanese Patent Application No. 2018-156407 filed on 23 Aug. 2018. The above application is hereby expressly incorporated by reference, in its entirety, into the present application.

BACKGROUND OF THE INVENTION

1. Field of the Invention

The present invention relates to a medical image processing apparatus, an endoscope system, and a method for operating the medical image processing apparatus that are for recognizing a region of interest such as a lesion portion.

2. Description of the Related Art

In the medical field, image diagnosis is performed for diagnosing a disease of a patient, performing follow-up, or the like by using a medical image such as an endoscopic image, an X-ray image, a computed tomography (CT) image, or a magnetic resonance (MR) image. A medical doctor or the like determines a course of treatment on the basis of such image diagnosis.

In recent years, image diagnosis using medical images has been employing a way of recognizing, by using a medical image processing apparatus, a region of interest to be carefully observed in a medical image, such as a lesion or a tumor in an organ. In particular, a method of machine learning such as deep learning contributes to improvement of recognition processing for a region of interest.

JP2016-158828A describes a medical image processing apparatus that performs recognition processing on individual medical images and that displays, in a case where a region of interest is recognized, a result of the recognition on a monitor or the like. In the medical image processing apparatus described in JP2016-158828A, either a graph in which a feature quantity of a medical image (a feature quantity of a region of interest) is plotted, or a label displaying text indicating the item name and value of a feature quantity of a medical image, is displayed near the region of interest of the medical image, and switching between graph display and label display is performed in response to input by a user.

SUMMARY OF THE INVENTION

When a medical doctor performs image diagnosis using a medical image, he/she is requested to observe not only a result of recognition processing performed on the medical image but also the medical image acquired by an imaging unit. However, in the medical image processing apparatus described in JP2016-158828A, when there are many recognition results displayed near a region of interest of a medical image, the recognition results may be overlapped with the medical image, which may disturb observation of the medical image.

An object of the present invention is to provide a medical image processing apparatus, an endoscope system, and a method for operating the medical image processing apparatus that prevent display of a recognition result obtained through recognition processing from hindering observation of a medical image.

A medical image processing apparatus of the present invention includes a medical image acquiring unit, a recognition processing unit, and a display control unit. The medical image acquiring unit acquires a medical image through imaging of an observation target. The recognition processing unit performs recognition processing on the medical image acquired by the medical image acquiring unit. The display control unit switches between a first display method in which the medical image acquired by the medical image acquiring unit is displayed in a display unit, and a second display method in which a plurality of recognition results are displayed in the display unit, the plurality of recognition results being obtained by performing the recognition processing on the medical image acquired by the medical image acquiring unit.

Preferably, the medical image processing apparatus may include an input unit that inputs an instruction to switch a display method to the display control unit.

Preferably, the display control unit may perform switching from the second display method to the first display method after a certain time period elapses from switching to the second display method.

Preferably, the display control unit may perform switching from the first display method to the second display method after a certain time period elapses from when the recognition processing unit ends the recognition processing.

Preferably, in a case of performing display on the display unit by using the second display method, the display control unit may display the medical image together with the plurality of recognition results.

Preferably, each of the plurality of recognition results may be a type of lesion. Preferably, each of the plurality of recognition results may be presence or absence of a lesion portion. Preferably, each of the plurality of recognition results may be a position of a lesion portion.

An endoscope system of the present invention includes a light source device, an endoscope, a medical image acquiring unit, a recognition processing unit, a display control unit, and a display unit. The light source device generates illumination light for illuminating an observation target. The endoscope has an imaging unit that performs imaging of the observation target illuminated with the illumination light. The medical image acquiring unit acquires a medical image through imaging of the observation target. The recognition processing unit performs recognition processing on the medical image acquired by the medical image acquiring unit. The display control unit switches between a first display method in which the medical image acquired by the medical image acquiring unit is displayed, and a second display method in which a plurality of recognition results are displayed, the plurality of recognition results being obtained by performing the recognition processing on the medical image acquired by the medical image acquiring unit. The display unit displays the medical image by using the first display method and the plurality of recognition results by using the second display method.

Preferably, the endoscope may include an input unit that inputs an instruction to switch a display method to the display control unit.

A method for operating a medical image processing apparatus of the present invention includes a step of, with a medical image acquiring unit, acquiring a medical image through imaging of an observation target; a step of, with a recognition processing unit, performing recognition processing on the medical image acquired by the medical image acquiring unit; and a step of, with a display control unit, switching between a first display method in which the medical image acquired by the medical image acquiring unit is displayed on a display unit, and a second display method in which a plurality of recognition results are displayed on the display unit, the plurality of recognition results being obtained by performing the recognition processing on the medical image acquired by the medical image acquiring unit.

According to the present invention, it is possible to prevent display of a recognition result obtained through recognition processing from hindering observation of a medical image.

BRIEF DESCRIPTION OF THE DRAWINGS

FIG. 7 is an explanatory diagram illustrating an example of display screens in a first display method (part (A)) and a second display method (part (B)) in a case where a display control unit performs switching control;

FIG. 10 is an explanatory diagram illustrating an example of display screens in the first display method (part (A)) and the second display method (part (B)) in a case where the display control unit performs switching control according to a third embodiment.

DESCRIPTION OF THE PREFERRED EMBODIMENTS

First Embodiment

Figure 1:
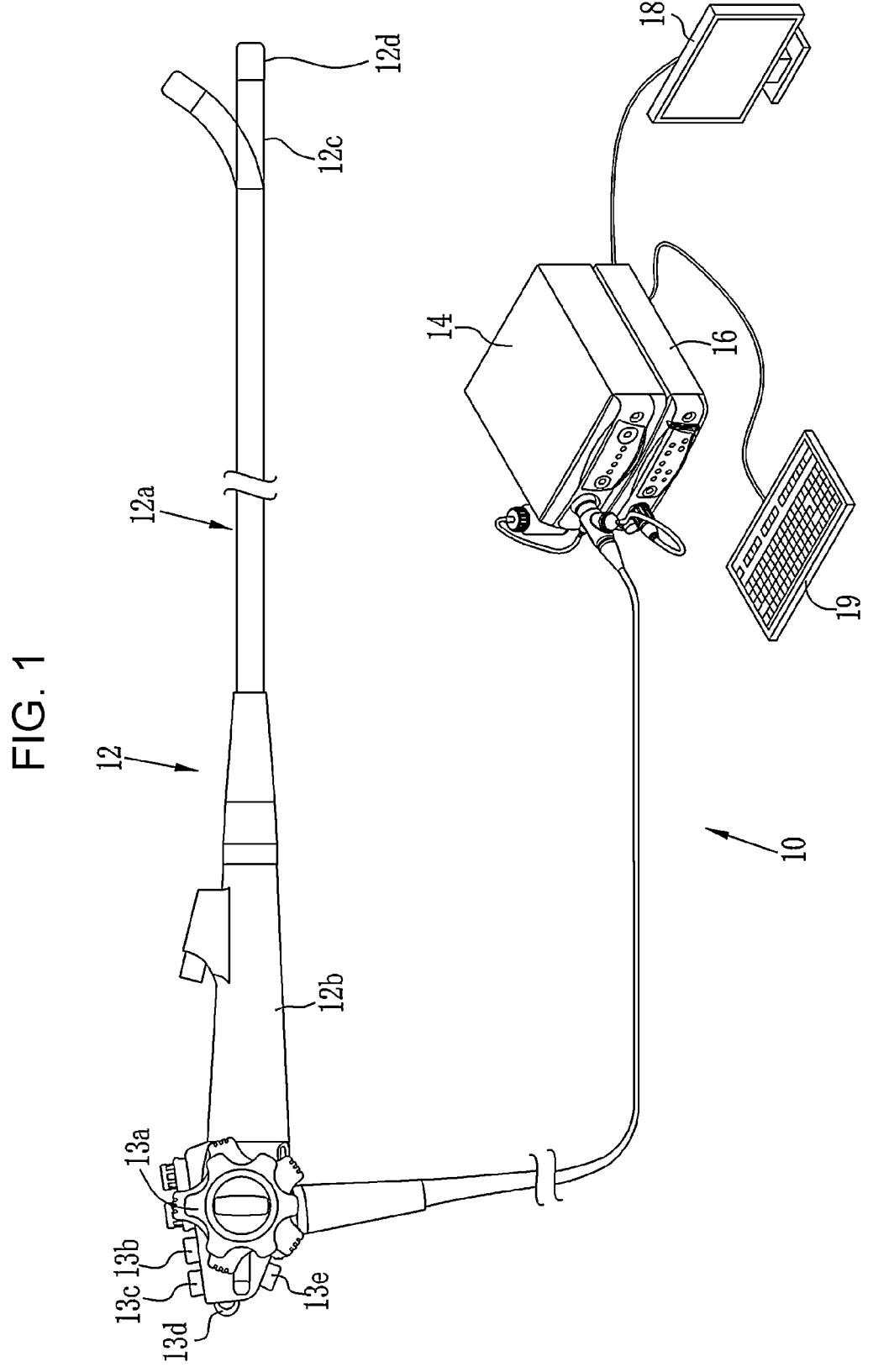
FIG. 1 is an external appearance diagram of an endoscope system.

As illustrated in FIG. 1, an endoscope system 10 has an endoscope 12, a light source device 14, a processor device 16, a monitor 18 (display unit), and a console 19. The endoscope 12 is optically connected to the light source device 14 and is electrically connected to the processor device 16. The endoscope 12 has an insertion section 12*a* to be inserted into a subject, an operation section 12*b* provided at a base end portion of the insertion section 12*a*, and a bending portion 12*c* and a distal end portion 12*d* that are provided on a distal end side of the insertion section 12*a*. Operating of an angle knob 13*a* of the operation section 12*b* causes the bending portion 12*c* to perform a bending operation. The bending operation causes the distal end portion 12*d* to be directed in a desired direction.

The operation section 12*b* is provided with, in addition to the angle knob 13*a*, a still image acquiring unit 13*b* to be used for an operation of acquiring a still image, a mode switching unit 13*c* to be used for an operation of switching an observation mode, a zoom operation unit 13*d* to be used for an operation of changing zoom magnification, and a display switching operation unit 13*e* serving as a dedicated input unit to be used to provide an instruction to switch a display method in a region-of-interest mode. The still image acquiring unit 13*b* is capable of performing a freeze operation of displaying a still image of an observation target on the monitor 18 and a release operation of storing a still image in storage.

The endoscope system 10 has a normal mode, a special mode, and a region-of-interest mode as observation modes. When the observation mode is the normal mode, normal light generated by combining light beams of a plurality of colors at a light amount ratio Lc for the normal mode is emitted. When the observation mode is the special mode, special light generated by combining light beams of a plurality of colors at a light amount ratio Ls for the special mode is emitted.

When the observation mode is the region-of-interest mode, illumination light for the region-of-interest mode is emitted. In this embodiment, normal light is emitted as the illumination light for the region-of-interest mode. Alternatively, special light may be emitted.

The processor device 16 is electrically connected to the monitor 18 and the console 19. The monitor 18 outputs and displays an image of an observation target, information accompanying the image, and so forth. The console 19 functions as a user interface that receives an input operation for designating a region of interest (ROI), setting a function, or the like.

Figure 2:
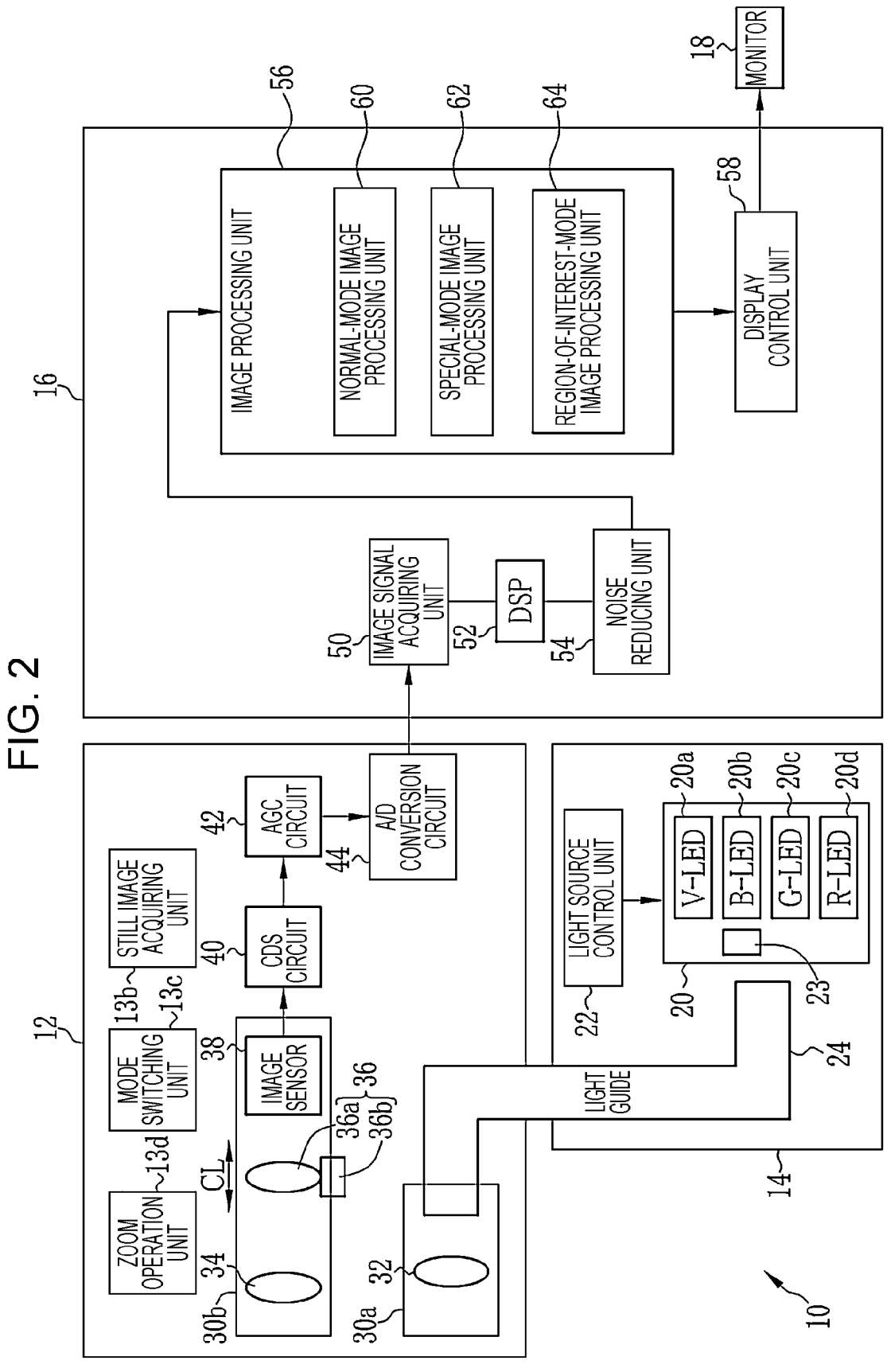
FIG. 2 is a block diagram illustrating the functions of the endoscope system according to a first embodiment including a plurality of LED light sources.

As illustrated in FIG. 2, the light source device 14 includes a light source unit 20 that emits illumination light to be used to illuminate an observation target, and a light source control unit 22 that controls the light source unit 20. The light source unit 20 is a semiconductor light source, such as light emitting diodes (LEDs) of a plurality of colors. The light source control unit 22 turns ON/OFF the LEDs or the like and adjusts driving currents and driving voltages for the LEDs or the like, thereby controlling the amount of illumination light to be emitted. In addition, the light source control unit 22 controls the wavelength range of the illumination light by, for example, changing an optical filter.

Figure 3:
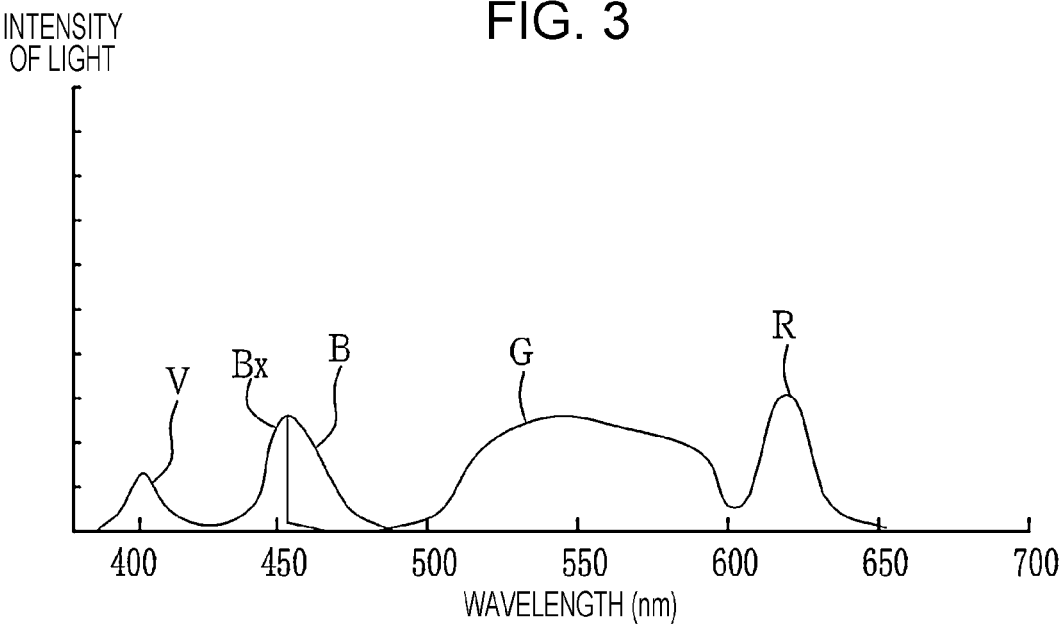
FIG. 3 is a graph illustrating a spectrum of violet light V, blue light B, blue light Bx, green light G, and red light R.

In the first embodiment, the light source unit 20 has LEDs of four colors: a violet light emitting diode (V-LED) 20*a*; a blue light emitting diode (B-LED) 20*b*; a green light emitting diode (G-LED) 20*c*; and a red light emitting diode (R-LED) 20*d*, and a wavelength cut filter 23. As illustrated in FIG. 3, the V-LED 20*a* emits violet light V in a wavelength range of 380 nm to 420 nm.

The B-LED 20*b* emits blue light B in a wavelength range of 420 nm to 500 nm. Of the blue light B emitted by the B-LED 20*b*, at least the longer wavelength side with respect to a peak wavelength of 460 nm is cut off by the wavelength cut filter 23. Accordingly, blue light Bx that has passed through the wavelength cut filter 23 is in a wavelength range of 420 nm to 460 nm. The light in the wavelength range on the longer wavelength side with respect to 460 nm is cut off because the light in the wavelength range on the longer wavelength side with respect to 460 nm is a factor in decreasing the contrast of blood vessels as an observation target. The wavelength cut filter 23 may decrease the amount of light in the wavelength range on the longer wavelength side with respect to 460 nm instead of cutting off the light in the wavelength range on the longer wavelength side with respect to 460 nm.

The G-LED 20c emits green light G in a wavelength range of 480 nm to 600 nm. The R-LED 20d emits red light R in a wavelength range of 600 nm to 650 nm. The light emitted by each of the LEDs 20a to 20d may have a center wavelength and a peak wavelength that are identical to or different from each other.

The light source control unit 22 controls ON/OFF of each of the LEDs 20a to 20d and the amount of light emission in an ON state independently from each other, thereby adjusting the emission timing, emission period, amount of light, and spectrum of illumination light. The ON/OFF control by the light source control unit 22 varies according to an observation mode. A reference brightness can be set by a brightness setting unit of the light source device 14, the console 19, or the like.

Figure 4:
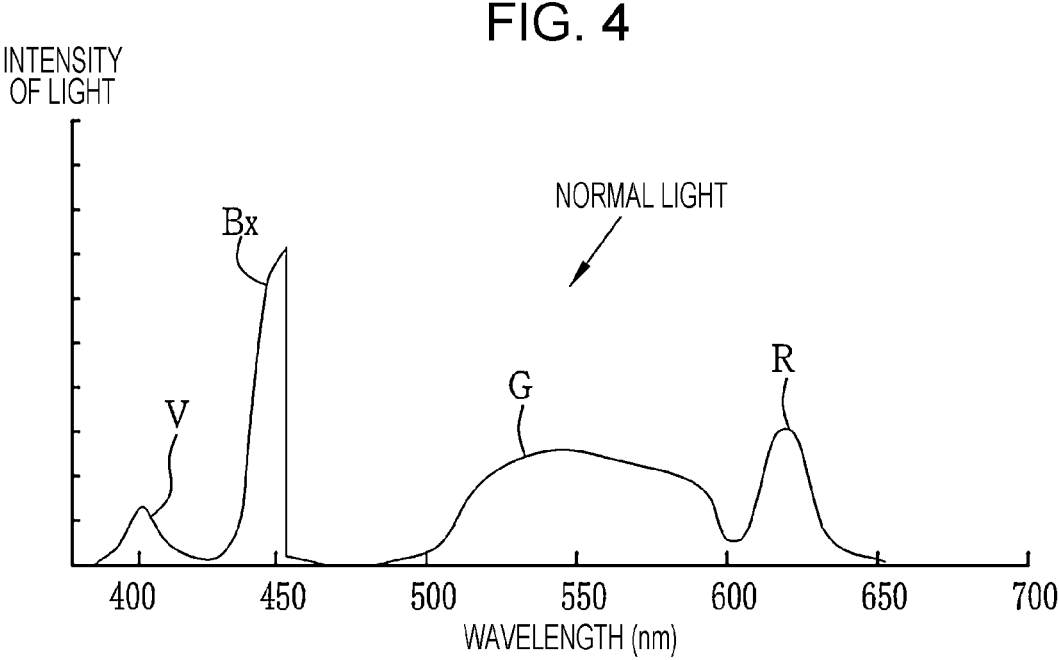
FIG. 4 is a graph illustrating a spectrum of normal light according to the first embodiment.

In the normal mode or the region-of-interest mode, the light source control unit 22 turns on all of the V-LED 20a, the B-LED 20b, the G-LED 20c, and the R-LED 20d. At this time, as illustrated in FIG. 4, the light amount ratio Lc among the violet light V, the blue light Bx, the green light G, and the red light R is set such that the peak intensity of the blue light Bx is higher than each of the peak intensities of the violet light V, the green light G, and the red light R. Accordingly, in the normal mode or the region-of-interest mode, the light source device 14 emits, as normal light, multicolor light for the normal mode or the region-of-interest mode including the violet light V, the blue light Bx, the green light G, and the red light R. The normal light has a certain intensity or more in the blue range to the red range and is thus substantially white.

Figure 5:
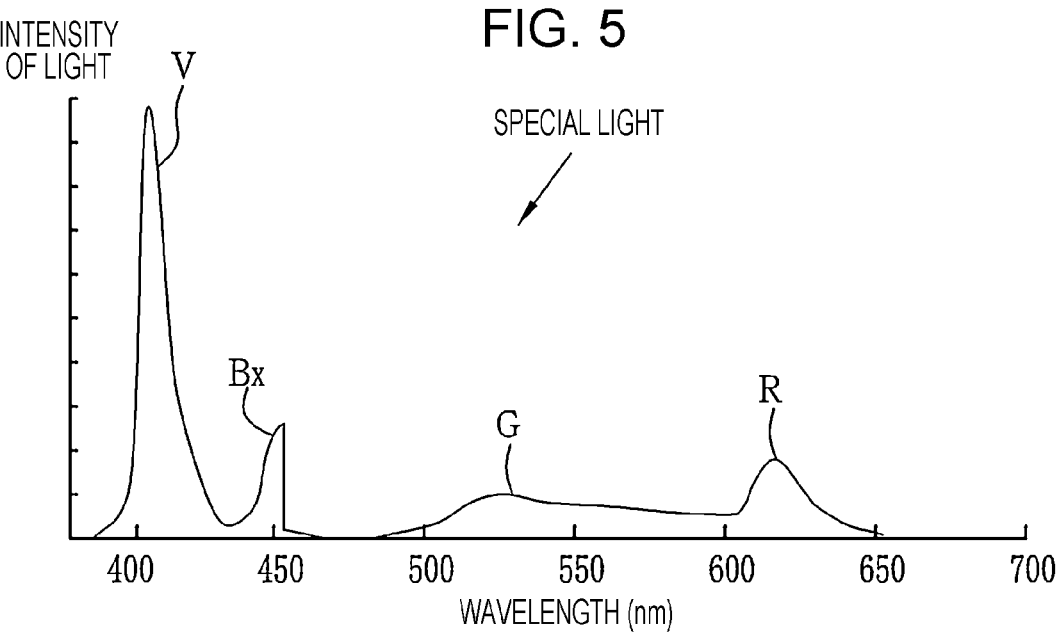
FIG. 5 is a graph illustrating a spectrum of special light according to the first embodiment.

In the special mode, the light source control unit 22 turns on all of the V-LED 20a, the B-LED 20b, the G-LED 20c, and the R-LED 20d. At this time, as illustrated in FIG. 5, the light amount ratio Ls among the violet light V, the blue light Bx, the green light G, and the red light R is set such that the peak intensity of the violet light V is higher than each of the peak intensities of the blue light Bx, the green light G, and the red light R and such that each of the peak intensities of the green light G and the red light R is lower than each of the peak intensities of the violet light V and the blue light Bx. Accordingly, in the special mode, the light source device 14 emits, as special light, multicolor light for the special mode including the violet light V, the blue light Bx, the green light G, and the red light R. The special light has a large proportion of the violet light V and is thus bluish. The special light does not necessarily need to include light of all the four colors, and may include light from at least one of the LEDs 20a to 20d of four colors. Preferably, the special light may have a main wavelength range, for example, a peak wavelength or a center wavelength, in a range that is 450 nm or less.

As illustrated in FIG. 2, the illumination light emitted by the light source unit 20 passes through a light path coupling unit (not illustrated) formed of a mirror, a lens, and the like and then enters a light guide 24 that extends through the insertion section 12a. The light guide 24 is built in the endoscope 12 and a universal cord, and causes the illumination light to propagate to the distal end portion 12d of the endoscope 12. The universal cord is a cord that connects the endoscope 12 to the light source device 14 and the processor device 16. A multimode fiber may be used as the light guide 24. As an example, a small-diameter fiber cable with a core diameter of 105 μm, a clad diameter of 125 μm, and a diameter including a protective layer serving as an outer cover of φ0.3 mm to φ0.5 mm may be used as the light guide 24.

The distal end portion 12d of the endoscope 12 is provided with an illumination optical system 30a and an imaging optical system 30b. The illumination optical system 30a has an illumination lens 32. An observation target is illuminated, via the illumination lens 32, with illumination light that has propagated through the light guide 24. The imaging optical system 30b has an objective lens 34, a magnifying optical system 36, and an image sensor 38 (corresponding to the "imaging unit" of the present invention). Various types of light, such as reflected light, scattered light, and fluorescence from the observation target, enters the image sensor 38 through the objective lens 34 and the magnifying optical system 36. Accordingly, an image of the observation target is formed on the image sensor 38.

The magnifying optical system 36 includes a zoom lens 36a that magnifies an observation target, and a lens driving unit 36b that moves the zoom lens 36a in optical-axis directions CL. The zoom lens 36a is freely moved between a telephoto end and a wide end in accordance with zoom control by the lens driving unit 36b, thereby magnifying or demagnifying the image of the observation target formed on the image sensor 38.

The image sensor 38 is a color image sensor that performs imaging of an observation target irradiated with illumination light. Each of the pixels of the image sensor 38 is provided with a red (R) color filter, a green (G) color filter, or a blue (B) color filter. The image sensor 38 receives violet to blue light by using B pixels provided with the B color filter, receives green light by using G pixels provided with the G color filter, and receives red light by using R pixels provided with the R color filter. The image sensor 38 outputs image signals of individual colors of RGB from the pixels of the individual colors. The image sensor 38 transmits the output image signals to a correlated double sampling (CDS) circuit 40.

In the normal mode or the region-of-interest mode, the image sensor 38 performs imaging of an observation target illuminated with normal light, thereby outputting Bc image signals from the B pixels, outputting Gc image signals from the G pixels, and outputting Rc image signals from the R pixels. In the special mode, the image sensor 38 performs imaging of an observation target illuminated with special light, thereby outputting Bs image signals from the B pixels, outputting Gs image signals from the G pixels, and outputting Rs image signals from the R pixels.

A charge coupled device (CCD) image sensor, a complementary metal-oxide semiconductor (CMOS) image sensor, or the like can be used as the image sensor 38. Instead of the image sensor 38 provided with color filters of the primary colors RGB, a complementary-color image sensor including complementary-color filters of cyan (C), magenta (M), yellow (Y), and green (G) may be used. In the case of using the complementary-color image sensor, image signals of four colors CMYG are output. Thus, as a result of converting image signals of four colors CMYG into image signals of three colors RGB by using complementary color to primary color conversion, image signals of individual colors RGB similar to those in the image sensor 38 can be acquired.

Alternatively, a monochrome sensor not provided with color filters may be used instead of the image sensor 38.

The CDS circuit 40 performs correlated double sampling (CDS) on analog image signals received from the image sensor 38. The image signals output from the CDS circuit 40 are input to an automatic gain control (AGC) circuit 42. The AGC circuit 42 performs automatic gain control (AGC) on the image signals input thereto. An analog to digital (A/D) conversion circuit 44 converts the analog image signals output from the AGC circuit 42 into digital image signals. The A/D conversion circuit 44 inputs the digital image signals generated through the A/D conversion to the processor device 16.

As illustrated in FIG. 2, the processor device 16 includes an image signal acquiring unit 50 (corresponding to the "medical image acquiring unit" of the present invention), a digital signal processor (DSP) 52, a noise reducing unit 54, an image processing unit 56, and a display control unit 58.

The image signal acquiring unit 50 acquires digital image signals corresponding to an observation mode from the endoscope 12. In the normal mode or the region-of-interest mode, the image signal acquiring unit 50 acquires Bc image signals, Gc image signals, and Rc image signals. In the special mode, the image signal acquiring unit 50 acquires Bs image signals, Gs image signals, and Rs image signals. In the region-of-interest mode, the image signal acquiring unit 50 acquires Bc image signals, Gc image signals, and Rc image signals of one frame during illumination with normal light, and acquires Bs image signals, Gs image signals, and Rs image signals of one frame during illumination with special light.

The DSP 52 performs various signal processing operations, such as defect correction processing, offset processing, DSP gain correction processing, linear matrix processing, gamma conversion processing, and demosaicing processing, on the image signals acquired by the image signal acquiring unit 50. The defect correction processing corrects a signal of a defective pixel of the image sensor 38. The offset processing removes a dark current component from the image signal that has been subjected to the defect correction processing and sets an accurate zero level. The DSP gain correction processing multiplies the image signal that has been subjected to the offset processing by a specific DSP gain, thereby adjusting the signal level.

The linear matrix processing increases the color reproducibility of the image signal that has been subjected to the DSP gain correction processing. The gamma conversion processing adjusts the brightness and chroma of the image signal that has been subjected to the linear matrix processing. The image signal that has been subjected to the gamma conversion processing is subjected to demosaicing processing (also referred to as isotropic processing or synchronization processing), thereby generating, through interpolation, a signal of a color insufficient in each pixel. The demosaicing processing enables all pixels to have signals of individual colors RGB. The noise reducing unit 54 performs noise reduction processing using, for example, a moving-average method, a median filter method, or the like, on the image signal that has been subjected to the demosaicing processing and so forth in the DSP 52, thereby reducing noise. The image signal that has been subjected to the noise reduction is input to the image processing unit 56.

The image processing unit 56 includes a normal-mode image processing unit 60, a special-mode image processing unit 62, and a region-of-interest-mode image processing unit 64. The normal-mode image processing unit 60 operates when the normal mode is set, and performs color conversion processing, color enhancement processing, and structure enhancement processing on the Bc image signals, Gc image signals, and Rc image signals that have been received. In the color conversion processing, color conversion processing is performed on the RGB image signals by using 3×3 matrix processing, gradation transformation processing, three-dimensional look up table (LUT) processing, and the like.

The color enhancement processing is performed on the RGB image signals that have been subjected to color conversion processing. The structure enhancement processing is processing of enhancing the structure of an observation target and is performed on the RGB image signals that have been subjected to the color enhancement processing. The above-described various image processing operations enable a normal image to be acquired. The normal image is an image acquired on the basis of normal light including the violet light V, the blue light Bx, the green light G, and the red light R with a well-balanced ratio, and is thus an image with natural colors. The normal image is input to the display control unit 58.

The special-mode image processing unit 62 operates when the special mode is set. The special-mode image processing unit 62 performs color conversion processing, color enhancement processing, and structure enhancement processing on the Bs image signals, Gs image signals, and Rs image signals that have been received. The processing performed in the color conversion processing, the color enhancement processing, and the structure enhancement processing is similar to that performed by the normal-mode image processing unit 60. The above-described various image processing operations enable a special image to be acquired. The special image is an image acquired on the basis of special light in which the amount of the violet light V having a high hemoglobin absorption coefficient of blood vessels is larger than the amount of the blue light Bx, the green light G, and the red light R, and thus the resolution of a blood vessel structure and a gland duct structure is higher than that of other structures. The special image is input to the display control unit 58.

The region-of-interest-mode image processing unit 64 operates when the region-of-interest mode is set. The region-of-interest-mode image processing unit 64 performs image processing similar to that performed by the normal-mode image processing unit 60, such as color conversion processing, on the Bc image signals, Gc image signals, and Rc image signals that have been received.

Figure 6:
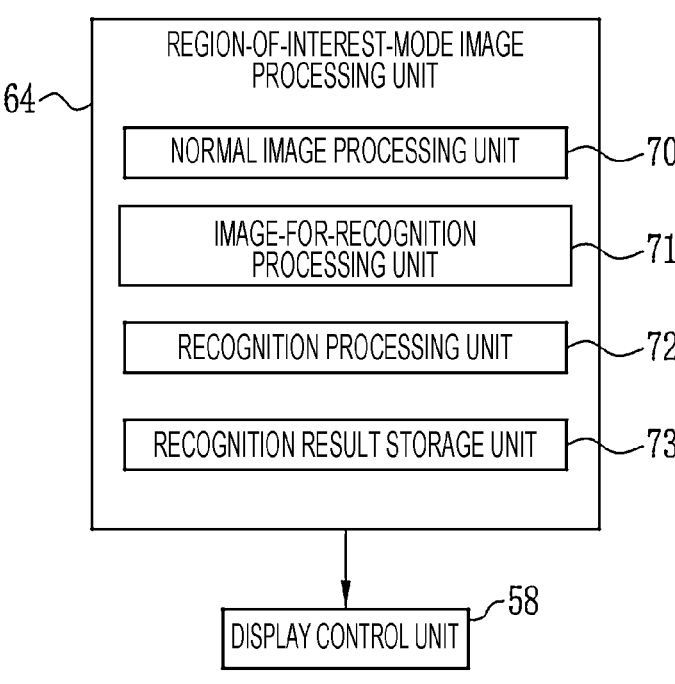
FIG. 6 is a block diagram illustrating the functions of a region-of-interest-mode image processing unit including a recognition processing unit.

As illustrated in FIG. 6, the region-of-interest-mode image processing unit 64 includes a normal image processing unit 70, an image-for-recognition processing unit 71, a recognition processing unit 72, and a recognition result storage unit 73. The normal image processing unit 70 performs image processing similar to that performed by the normal-mode image processing unit 60, thereby sequentially acquiring endoscopic images. On the other hand, the image-for-recognition processing unit 71 acquires a still image of an observation target obtained when the still image acquiring unit 13*b* is operated, as an image for recognition to be used for recognizing a region of interest. The image for recognition is stored in the recognition result storage unit 73.

The recognition processing unit 72 analyzes an image for recognition and performs recognition processing. The recognition processing performed by the recognition processing unit 72 includes detection processing of detecting a region of interest from an image for recognition and discrimination processing of discriminating the type or the like of a lesion included in the image for recognition. Specifically, in the discrimination processing, a discrimination result of a region of interest may be output, or a discrimination result of the entire image for recognition may be output. In this embodiment, the recognition processing unit 72 performs detection processing of detecting a lesion portion which is a region of interest from an image for recognition. In this case, the recognition processing unit 72 first divides the image for recognition into a plurality of small regions, for example, square regions each formed of a certain number of pixels. Subsequently, the recognition processing unit 72 calculates image feature quantities from the divided image for recognition. Subsequently, the recognition processing unit 72 determines, on the basis of the calculated feature quantities, whether or not each of the small regions is a lesion portion. Preferably, such a determination method may be a machine learning algorithm such as a convolutional neural network or deep learning.

Preferably, a feature quantity calculated from an image for recognition by the recognition processing unit 72 may be the shape or color of a predetermined portion in an observation target, or an index value acquired from the shape or color. Preferably, for example, the feature quantity may be at least any one of the density of a blood vessel, the shape of a blood vessel, the number of branches of a blood vessel, the thickness of a blood vessel, the length of a blood vessel, the degree of meandering of a blood vessel, the depth of a blood vessel, the shape of a gland duct, the shape of an opening portion of a gland duct, the length of a gland duct, the degree of meandering of a gland duct, or color information, or the value of a combination of two or more of them.

Finally, the recognition processing unit 72 extracts a group of small regions specified as the same type as one lesion portion. The recognition processing unit 72 stores information indicating the presence or absence of the lesion portion in the recognition result storage unit 73 in association with the image for recognition. The region-of-interest-mode image processing unit 64 outputs, in accordance with control by the display control unit 58, either the endoscopic image or the image for recognition associated with the information indicating the presence or absence of the lesion portion to the display control unit 58.

The display control unit 58 performs display control for displaying an image or data from the image processing unit 56 on the monitor 18. When the normal mode is set, the display control unit 58 performs control to display a normal image on the monitor 18. When the special mode is set, the display control unit 58 performs control to display a special image on the monitor 18.

Figure 7:
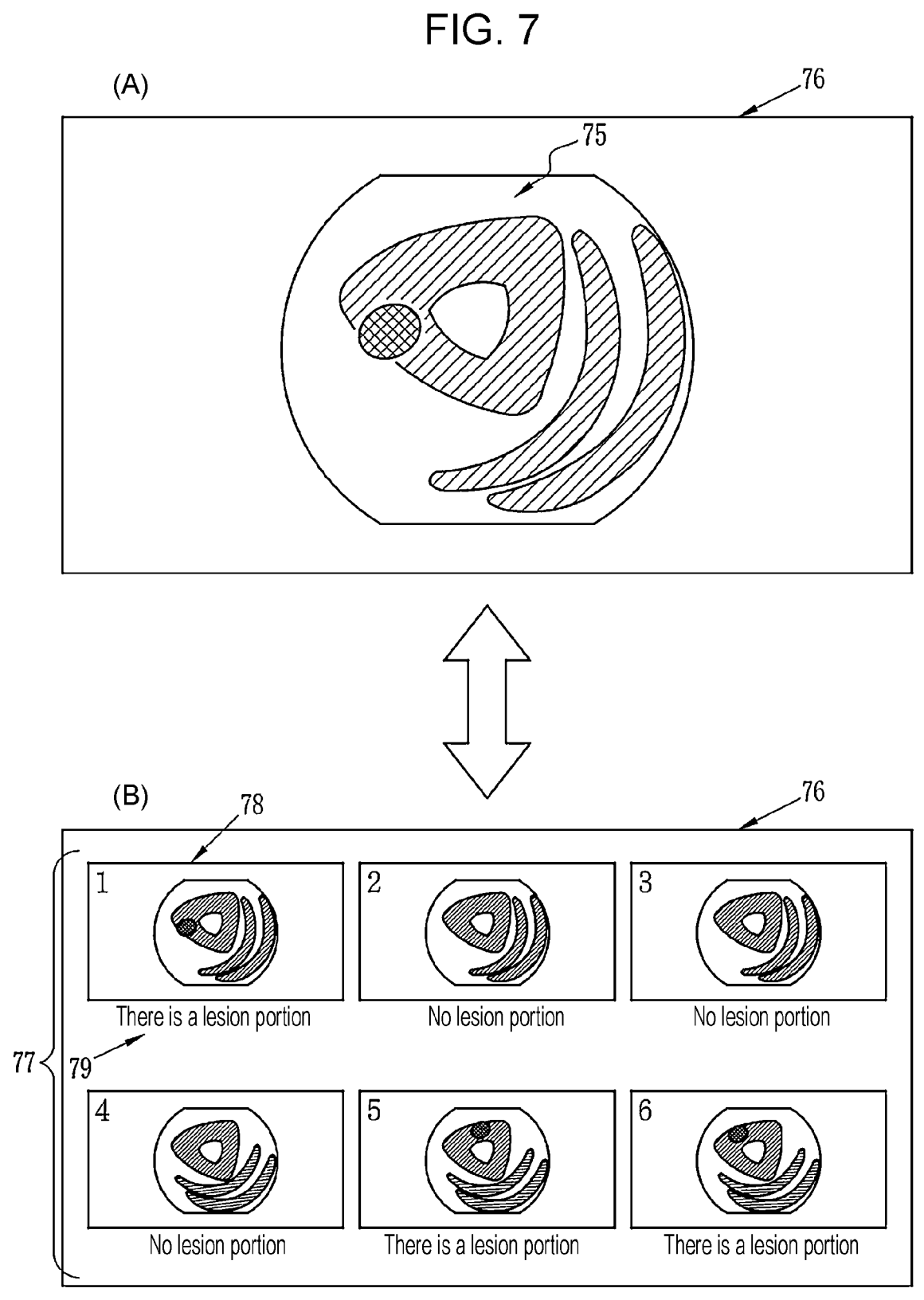

When the region-of-interest mode is set, the display control unit 58 switches between a first display method and a second display method. An instruction to switch the display method to the display control unit 58 is input by operating the display switching operation unit 13e. As illustrated in part (A) of FIG. 7, the first display method is a display method of sequentially acquiring endoscopic images 75 (images similar to normal images) captured by the image sensor 38 and processed by the region-of-interest-mode image processing unit 64 and displaying the endoscopic images 75 in real time on a display screen 76 of the monitor 18.

On the other hand, the second display method is a display method of displaying a plurality of recognition results on the display screen 76 of the monitor 18, the recognition results being obtained through recognition processing performed on images for recognition by the recognition processing unit 72. Specifically, as illustrated in part (B) of FIG. 7, in the second display method, a recognition result list 77 is displayed on the display screen 76 of the monitor 18, the recognition result list 77 including thumbnail images 78 of a plurality of images for recognition and lesion portion presence/absence labels 79 as recognition results corresponding to the respective images for recognition. In this case, the display control unit 58 displays the thumbnail images 78 and the lesion portion presence/absence labels 79 on the basis of the images for recognition output from the region-of-interest-mode image processing unit 64 and information indicating the presence or absence of a lesion portion associated with the images for recognition. Each lesion portion presence/absence label 79 is displayed near the thumbnail image 78 of the corresponding image for recognition. In the example illustrated in part (B) of FIG. 7, six thumbnail images 78 and six lesion portion presence/absence labels 79 as recognition results are displayed as the recognition result list 77. Alternatively, the number and disposition of images and recognition results to be displayed may be appropriately changed in accordance with the size, aspect ratio, or the like of the display screen and images. Also in the following embodiments, the number and disposition of images and recognition results are not limited.

In the thumbnail images 78 displayed as a recognition result list, the region of the lesion portion extracted by the recognition processing unit 72 may be displayed, for example, with the color, gradation, or the like thereof being changed. In a case where any one of the thumbnail images 78 is selected through input in the console 19, the original image for recognition may be displayed.

Figure 8:
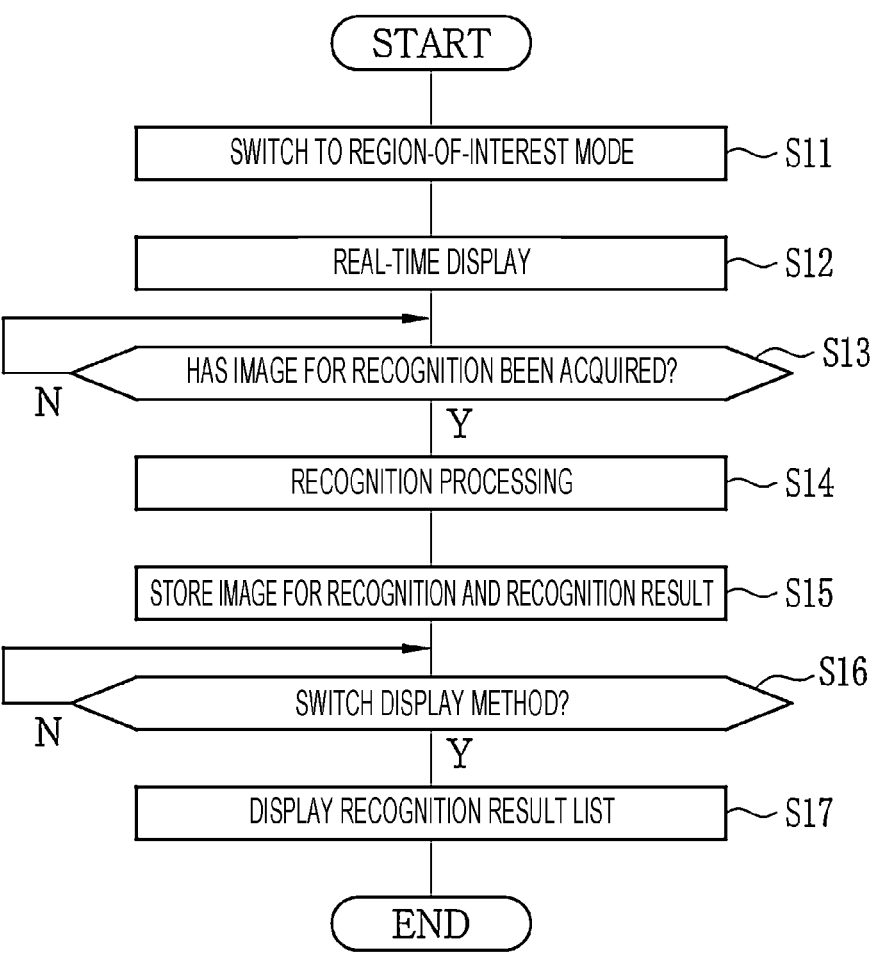
FIG. 8 is a flowchart illustrating a flow of a region-of-interest mode.

Next, a flow of the region-of-interest mode will be described with reference to the flowchart illustrated in FIG. 8. A medical doctor who is a user operates the mode switching unit 13c to switch the mode to the region-of-interest mode (S11). Accordingly, an observation target is irradiated with illumination light for the region-of-interest mode. The image sensor 38 performs imaging of the observation target irradiated with the illumination light for the region-of-interest mode, and thereby an endoscopic image is acquired. In this embodiment, the first display method is set in an initial state of the display control unit 58. Thus, upon switching to the region-of-interest mode, the endoscopic image 75 is displayed on the display screen 76 of the monitor 18 in real time (S12). In this case, only the endoscopic image 75 is displayed and a recognition result is not displayed on the display screen 76. Thus, observation of the endoscopic image 75 by the medical doctor is not hindered.

During the real-time display in the first display method, the medical doctor who is observing the endoscopic image operates the still image acquiring unit 13b to acquire an image for recognition (S13). In a case where the image for recognition has been acquired, recognition processing for detecting a lesion portion is performed on the image for recognition (S14). A recognition result obtained through the recognition processing is stored in the recognition result storage unit 73 in association with the image for recognition (S15).

Subsequently, when the medical doctor inputs an instruction to switch the display method by using the display switching operation unit 13e, the display control unit 58 switches the display method from the first display method to the second display method (S16). Upon switching to the second display method, the recognition result list 77 is displayed on the display screen 76 of the monitor 18 (S17). The lesion portion presence/absence labels 79 as recognition results are displayed in a list view together with the thumbnail images 78 of the images for recognition, and thus the medical doctor is able to easily check the recognition results of regions of interest.

When the endoscopic image 75 is to be observed again after checking the recognition results of regions of interest, the medical doctor inputs an instruction to switch the display method by using the display switching operation unit 13e. Accordingly, the display control unit 58 switches the display method from the second display method to the first display method and displays the endoscopic image 75 on the display screen 76 of the monitor 18 in real time. The display switching operation unit 13e for inputting an instruction to switch the display method is provided on the endoscope 12, and thus the medical doctor is able to easily switch between the first and second display methods.

Second Embodiment

Figure 9:
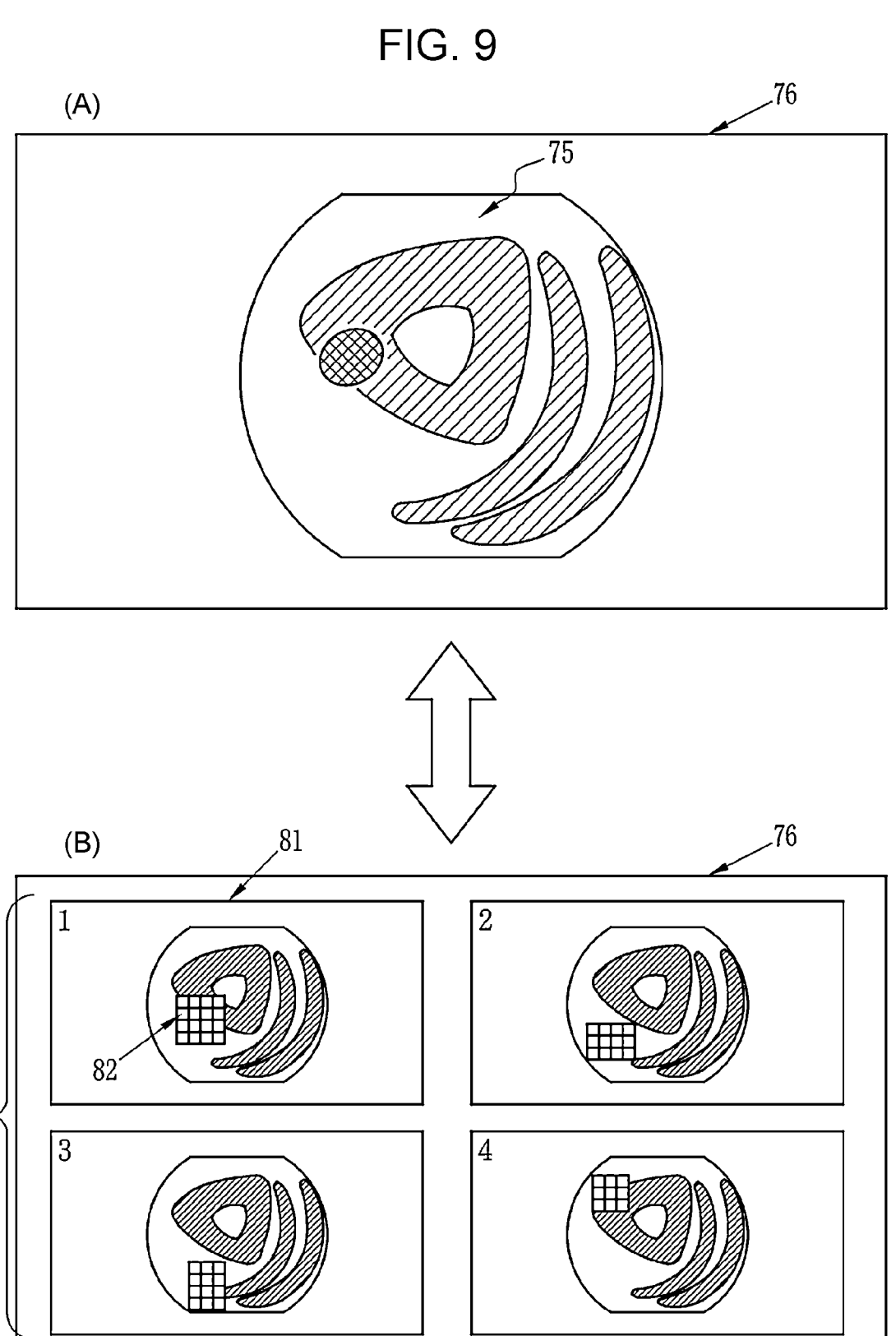
FIG. 9 is an explanatory diagram illustrating an example of display screens in the first display method (part (A)) and the second display method (part (B)) in a case where the display control unit performs switching control according to a second embodiment.

In the above-described first embodiment, lesion portion presence/absence labels are displayed as recognition results in the recognition result list in the second display method. Alternatively, lesion portion position labels may be displayed as recognition results. Specifically, as illustrated in part (B) of FIG. 9, in a recognition result list 80, thumbnail images 81 of a plurality of images for recognition and lesion portion position labels 82 as recognition results corresponding to the respective images for recognition are displayed on the display screen 76 of the monitor 18. In the first display method, as illustrated in part (A) of FIG. 9, the endoscopic images 75 are sequentially acquired and displayed on the monitor 18 in real time as in the first embodiment. The switching of the display method is similar to that in the region-of-interest mode in the above-described first embodiment except that lesion portion position labels are displayed in the second display method.

In this case, the recognition processing unit 72 divides the image for recognition into a plurality of small regions, as in the first embodiment. Subsequently, the recognition processing unit 72 calculates image feature quantities from the divided image for recognition, and determines whether or not each of the small regions is a lesion portion on the basis of the calculated feature quantities. Subsequently, the recognition processing unit 72 extracts position information of each small region determined to be a lesion portion, for example, coordinate information in the image for recognition. The recognition processing unit 72 stores the extracted coordinate information of the lesion portion in the recognition result storage unit 73 in association with the image for recognition. The region-of-interest-mode image processing unit 64 outputs, in accordance with control by the display control unit 58, either the endoscopic image or the image for recognition associated with the recognition result to the display control unit 58 as in the first embodiment.

In the case of performing the second display method, the display control unit 58 displays the thumbnail images 78 of the images for recognition and the lesion portion position labels 82 as recognition results on the display screen 76 of the monitor 18 on the basis of the images for recognition and coordinate information associated with the images for recognition. In part (B) of FIG. 9, each lesion portion position label 82 is shown by displaying the individual small regions recognized as a lesion portion by using a matrix of squares. Alternatively, any display manner may be used as long as the lesion portion position label 82 is recognized, for example, the color or gradation may be changed. Alternatively, text information representing coordinate information using characters may be used.

In the above-described first and second embodiments, images for recognition (including thumbnail images) and recognition results displayed in the recognition result list in the second display method are based on previous endoscopic images, that is, obtained by performing recognition processing on endoscopic images acquired as the image for recognition when the still image acquiring unit 13b is operated. Alternatively, a recognition result based on the latest endoscopic image acquired through imaging performed by the image sensor 38 may be included in the recognition result list. In this case, while the image sensor 38 is sequentially acquiring endoscopic images in the region-of-interest mode, recognition processing is constantly performed on the endoscopic images.

Recognition processing is constantly performed on the latest endoscopic images that are sequentially acquired to acquire recognition results. Preferably, the images for recognition and recognition results displayed in the recognition result list in the second display method may include those based on the latest endoscopic image acquired by the image sensor 38. Furthermore, in this case, it is preferable that the recognition result list in the second display method be displayed such that the image for recognition and the recognition result based on the latest endoscopic image are placed at the top (the image for recognition and the recognition result denoted by a number "1" in part (B) of FIG. 7 or part (B) of FIG. 9) and thereafter the images for recognition and the recognition results acquired through previous recognition processing are arranged in reverse chronological order, from a new one to an old one (the images for recognition and the recognition results denoted by numbers "2", "3", "4", and the like in part (B) of FIG. 7 or part (B) of FIG. 9).

Recognition processing is not necessarily performed on all the endoscopic images sequentially acquired by the image sensor 38. Thinned-out processing may be performed, that is, images for recognition may be acquired at predetermined time intervals or every predetermined frames from among all the endoscopic images, and recognition processing may be performed on the thinned out images for recognition to acquire recognition results.

Third Embodiment

In the above-described first and second embodiments, in the case of performing display by using the second display method, only a recognition result list is displayed. Alternatively, an endoscopic image may be displayed in real time together with the recognition result list. In the first display method, the endoscopic images 75 are sequentially acquired and displayed on the monitor 18 in real time as in the first embodiment, as illustrated in part (A) of FIG. 10.

Figure 10:
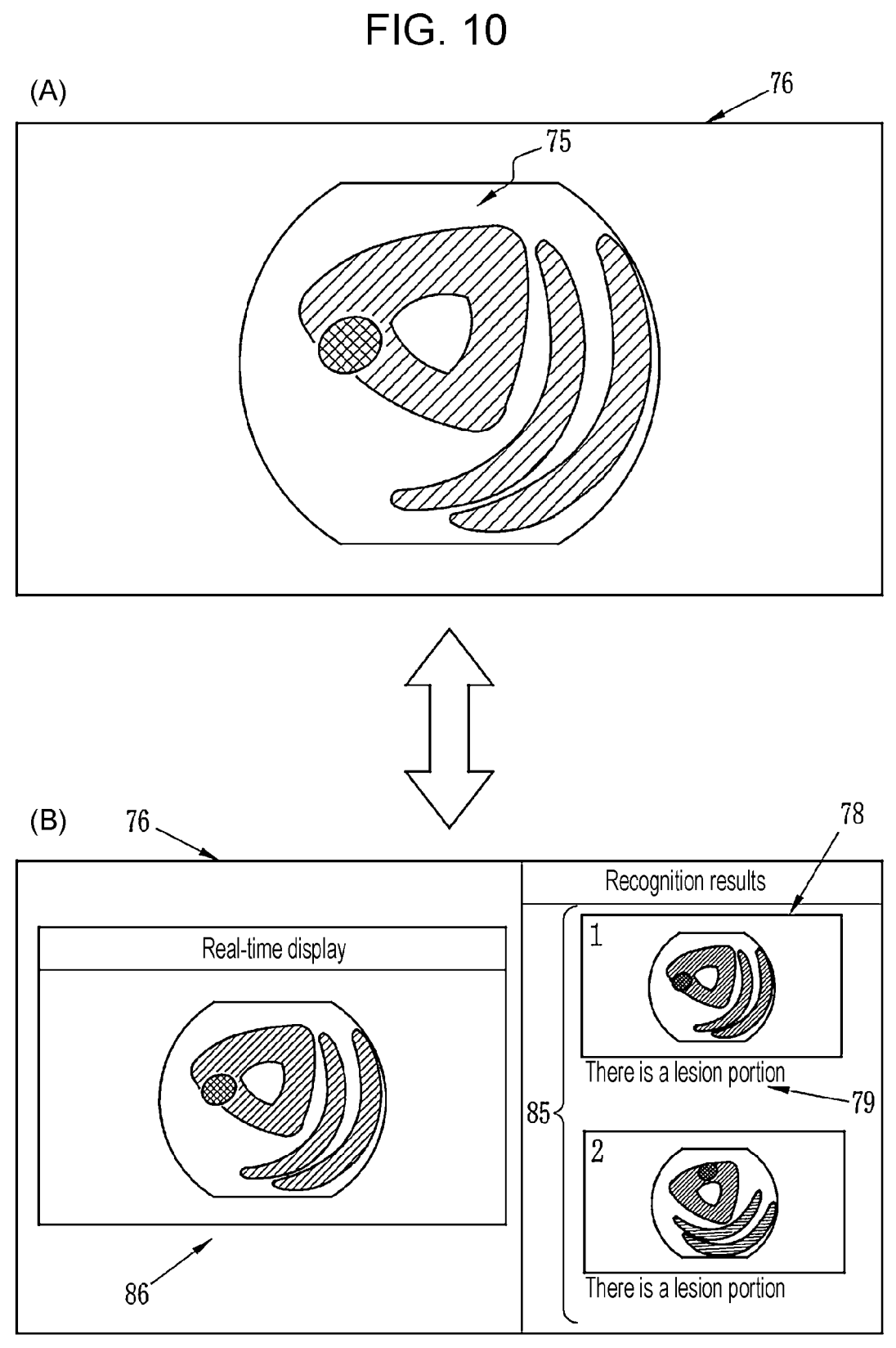

As illustrated in part (B) of FIG. 10, in the second display method, an endoscopic image 86 is displayed in real time together with a recognition result list 85 similar to that in the first embodiment. In this case, the recognition processing unit 72 performs recognition processing in a manner similar to that in the first embodiment. The recognition processing unit 72 stores information indicating the presence or absence of a detected lesion portion in the recognition result storage unit 73 in association with an image for recognition. The region-of-interest-mode image processing unit 64 outputs, in accordance with control by the display control unit 58, only the endoscopic image or both the endoscopic image and the image for recognition associated with the recognition result to the display control unit 58.

In the case of performing the second display method, the display control unit 58 displays the real-time endoscopic image 86 on the display screen 76 of the monitor 18, together with the recognition result list 85 including the thumbnail images 78 of the images for recognition and the lesion portion presence/absence labels 79 as recognition results, on the basis of the endoscopic image, the images for recognition, and information associated with the images for recognition. In the real-time display in the second display method, the endoscopic images 86 that are captured by the image sensor 38 and processed by the region-of-interest-mode image processing unit 64 are sequentially acquired and displayed in real time, as in the first display method. In part (B) of FIG. 10, lesion portion presence/absence labels are displayed as recognition results as in the first embodiment. Alternatively, lesion portion position labels may be displayed as recognition results as in the second embodiment.

In each of the above-described embodiments, a result of detection processing performed on a lesion portion by the recognition processing unit 72 is displayed as a recognition result in the second display method. Alternatively, a result of discrimination processing performed by the recognition processing unit 72 may be displayed as a recognition result. That is, the recognition processing unit 72 may detect a lesion portion from an image for recognition as in each of the above-described embodiments, and may perform discrimination processing of discriminating the type of lesion or the like on the detected lesion portion or perform discrimination processing on the entire image for recognition, thereby displaying a discrimination result. Preferably, the discrimination processing by the recognition processing unit 72 may be performed by using artificial intelligence (AI), deep learning, convolutional neural network, template matching, texture analysis, frequency analysis, or the like.

Specifically, the display control unit 58 may cause the type of lesion discriminated by the recognition processing unit 72 to be displayed as a recognition result in the second display method. In this case, for example, it is preferable that the types of lesions discriminated by the recognition processing unit 72 be predetermined according to the portion to be diagnosed. For example, in diagnosis of the large intestine, the portion to be discriminated is classified to any one of normal, hyperplastic polyp (HP), sessile serrated adenoma/polyp (SSA/P), traditional serrated adenoma (TSA), laterally spreading tumor (LST), and cancer. The types of lesions to be discriminated may be set by input in the console 19, for example.

In each of the above-described embodiments, the display switching operation unit 13e for inputting an instruction to switch the display method to the display control unit 58 is provided on the endoscope 12. Alternatively, any input unit for inputting an instruction to switch the display method to the display control unit 58 may be used. For example, an input unit having a similar function of inputting a switching instruction may be provided in the medical image processing apparatus.

In each of the above-described embodiments, an example is illustrated in which the display method is switched from the first display method to the second display method and then a switching instruction is input again by using the input unit to return the display method to the first display method. Alternatively, the display control unit 58 may switch the display method from the second display method to the first display method after a certain time period elapses from switching to the second display method. In this case, the certain time period from the switching to the second display method to the switching to the first display method may be a time period sufficient for a medical doctor as a user to check a recognition result and may be set in advance. Alternatively, the time period from the switching to the second display method to the switching to the first display method may be set by using, for example, input in the console 19.

In each of the above-described embodiments, an example is illustrated in which the display method is switched from the first display method to the second display method in response to an instruction of the input unit. Alternatively, the display control unit 58 may switch the display method from the first display method to the second display method after a certain time period elapses from when the recognition processing unit 72 ends the recognition processing. In this case, it is preferable to perform recognition processing and switch the display method from the first display method to the second display method every time a still image of an observation target is acquired as an image for recognition when the still image acquiring unit 13b is operated. The certain time period from the end of the recognition processing to the switching from the first display method to the second display method may be a time period sufficient for the display control unit 58 to create an image of a recognition result list and display a display screen after the recognition processing performed by the recognition processing unit 72 and may be set in advance. Alternatively, the time period to the switching from the first display method to the second display method may be set by using, for example, input in the console 19.

Although an observation target is illuminated by using the four-color LEDs 20a to 20d in each of the above-described embodiments, the observation target may be illuminated by using a laser light source and a fluorescent body. Although an observation target is illuminated by using the four-color LEDs 20a to 20d in each of the above-described embodiments, the observation target may be illuminated by using a white light source such as a xenon lamp and a rotary filter. Imaging of an observation target may be performed by using a monochrome image sensor instead of the color image sensor 38.

In the above-described embodiments, the medical image processing apparatus of the present invention is applied to an endoscope system that acquires an endoscopic image as a medical image. Obviously, the medical image processing apparatus of the present invention can be applied to various types of endoscope systems, such as a capsule endoscope. Also, the medical image processing apparatus of the present invention can be applied to various types of medical image apparatuses that acquire other types of medical images, such as an X-ray image, a CT image, an MR image, an ultrasound image, a pathological image, and a positron emission tomography (PET) image.

In the above-described embodiments, the hardware structure of a processing unit that executes various processing operations, such as the image processing unit 56, may be various types of processors described below. The various types of processors include a central processing unit (CPU), which is a general-purpose processor executing software (program) and functioning as various processing units; a graphical processing unit (GPU); a programmable logic device (PLD), which is a processor whose circuit configuration is changeable after manufacturing, such as a field programmable gate array (FPGA); a dedicated electric circuit, which is a processor having a circuit configuration designed exclusively for executing various processing operations, and the like.

A single processing unit may be constituted by one of these various types of processors or may be constituted by a combination of two or more processors of the same type or different types (for example, a combination of a plurality of FPGAs, a combination of a CPU and an FPGA, or a combination of a CPU and a GPU). A plurality of processing units may be constituted by a single processor. Examples of constituting a plurality of processing units by a single processor are as follows. First, as represented by a computer of a client or server, a single processor is constituted by a combination of one or more CPUs and software, and the processor functions as a plurality of processing units. Secondly, as represented by a system on chip (SoC), a processor in which a single integrated circuit (IC) chip implements the function of an entire system including a plurality of processing units is used. In this way, various types of processing units are constituted by using one or more of the above-described various types of processors as a hardware structure.

Furthermore, the hardware structure of these various types of processors is, more specifically, electric circuitry including a combination of circuit elements, such as semiconductor elements.

REFERENCE SIGNS LIST 10 endoscope system
12 endoscope
12a insertion section
12b operation section
12c bending portion
12d distal end portion
13a angle knob
13b still image acquiring unit
13c mode switching unit
13d zoom operation unit
14 light source device
16 processor device
18 monitor
9 console
20 light source unit
20a V-LED
20b B-LED
20c G-LED
20d R-LED
22 light source control unit
23 wavelength cut filter
24 light guide
30a illumination optical system
30b imaging optical system
32 illumination lens
34 objective lens
36 magnifying optical system
36a zoom lens
36b lens driving unit
38 image sensor
40 CDS circuit
42 AGC circuit
44 A/D conversion circuit
50 image signal acquiring unit
52 DSP
54 noise reducing unit
56 image processing unit
58 display control unit
60 normal-mode image processing unit
62 special-mode image processing unit
64 region-of-interest-mode image processing unit
70 normal image processing unit
71 image-for-recognition processing unit
72 recognition processing unit
73 recognition result storage unit 75 endoscopic image
76 display screen
77 recognition result list
78 thumbnail image
79 lesion portion presence/absence label
80 recognition result list
81 thumbnail image
82 lesion portion position label
85 recognition result list
86 endoscopic image

What is claimed is:

1. A medical image processing apparatus comprising:
a processor configured to function as:
a medical image acquiring unit that sequentially acquires endoscopic images through imaging of an observation target;
a recognition processing unit that performs recognition processing on the endoscopic images sequentially acquired by the medical image acquiring unit, wherein the recognition processing unit acquires a still image as an image for recognition and executes the recognition processing on the image for recognition, in response to a still image acquiring instruction input by a user; and
a display control unit that switches, in response to a switching display instruction input by the user, between a first display method in which the endoscopic images sequentially acquired by the medical image acquiring unit is displayed in real time on a display but a recognition result by the recognition processing is not displayed on any display, and a second display method in which the recognition result obtained based on one of the endoscopic images displayed by the first display method is displayed on the display and the first display method is not displayed on any display, the recognition result being obtained by performing the recognition processing on the endoscopic image displayed by the first display method and acquired by the medical image acquiring unit, wherein, in the second display method, a plurality of recognition results which includes the recognition result is displayed in a list format, each recognition result of the plurality of recognition results includes a thumbnail image and a corresponding lesion-information label.

2. The medical image processing apparatus according to claim 1, further comprising an input device that inputs the switching display instruction to switch between the first display method and the second display method to the display control unit.

3. The medical image processing apparatus according to claim 1, wherein the display control unit performs switching from the second display method to the first display method after a certain time period elapses from switching to the second display method.

4. The medical image processing apparatus according to claim 1, wherein the display control unit performs switching from the first display method to the second display method after a certain time period elapses from when the recognition processing unit ends the recognition processing.

5. The medical image processing apparatus according to claim 1, wherein in a case of performing display on the display by using the second display method, the display control unit displays the endoscopic images together with the plurality of recognition results.

6. The medical image processing apparatus according to claim 5, wherein each of the plurality of recognition results is a type of lesion.

7. The medical image processing apparatus according to claim 5, wherein each of the plurality of recognition results is presence or absence of a lesion portion.

8. The medical image processing apparatus according to claim 5, wherein each of the plurality of recognition results is a position of a lesion portion.

9. The medical image processing apparatus according to claim 8, wherein, in the second display method, a plurality of the endoscopic images subjected to the recognition processing is displayed side by side on the display, and a rectangular frame indicating the position of the lesion portion is overlaid on each of the displayed endoscopic images, in a manner that the plurality of the endoscopic images are comparable with the position of the lesion portion in each of the displayed endoscopic image.

10. The medical image processing apparatus according to claim 1, wherein, in the second display method, the endoscopic images are displayed in real-time in addition to the recognition result.

11. The medical image processing apparatus according to claim 1, further comprising multiple light sources with different emission colors, and wherein the endoscopic images are obtained by illuminating the observation target with combined illumination light, which is a blend of light from each emission color in a predetermined ratio of light amounts.

12. The medical image processing apparatus according to claim 11, wherein as the endoscopic images, a normal image and a special image are acquired, the normal image being imaged by illuminating the observation target with normal light at a first light amount ratio, and the special image being imaged by illuminating the observation target with special light at a second light amount ratio different from the first light amount ratio.

13. The medical image processing apparatus according to claim 12, wherein, in the first display method, the special image is displayed as one of the endoscopic images, and in the second display method, the result of the recognition processing performed on the special image is displayed as the recognition result.

14. An endoscope system comprising:
a light source device that generates illumination light for illuminating an observation target;
an endoscope having an imaging device that performs imaging of the observation target illuminated with the illumination light; and
a processor configured to function as:
a medical image acquiring unit that sequentially acquires endoscopic images through imaging of the observation target;
a recognition processing unit that performs recognition processing on the endoscopic images sequentially acquired by the medical image acquiring unit, wherein the recognition processing unit acquires a still image as an image for recognition and executes the recognition processing on the image for recognition, in response to a still image acquiring instruction input by a user; and
a display control unit that switches, in response to a switching display instruction input by the user, between a first display method in which the endoscopic images sequentially acquired by the medical image acquiring unit is displayed in real time on a display but a recognition result by the recognition processing is not displayed on any display, and a second display method in which the recognition result obtained based on one of the endoscopic images displayed by the first display method is displayed and the first display method is not displayed on any display, a plurality of recognition results including the recognition result being obtained by performing the recognition processing on the endoscopic image displayed by the first display method and acquired by the medical image acquiring unit; and
a display that displays the endoscopic images by using the first display method and the plurality of recognition results by using the second display method, wherein, in the second display method, the plurality of recognition results which includes the recognition result is displayed in a list format, each recognition result of the plurality of recognition results includes a thumbnail image and a corresponding lesion-information label.

15. The endoscope system according to claim 14, wherein the endoscope comprises an input device that inputs the switching display instruction to switch between a first display method and a second display method to the display control unit.

16. A method for operating a medical image processing apparatus having processor, the steps executed by the processor comprising:
sequentially acquiring endoscopic images through imaging of an observation target;
performing recognition processing on the endoscopic images sequentially acquired by a medical image acquiring unit, wherein the recognition processing unit acquires a still image as an image for recognition and executes the recognition processing on the image for recognition, in response to a still image acquiring instruction input by a user; and
switching, in response to a switching display instruction input by the user, between a first display method in which the endoscopic images sequentially acquired by the medical image acquiring unit is displayed in real time on a display but a recognition result by the recognition processing is not displayed on any display, and a second display method in which the recognition result obtained based on one of the endoscopic images displayed by the first display method is displayed on the display and the first display method is not displayed on any display, the recognition result being obtained by performing the recognition processing on the endoscopic image displayed by the first display method and acquired by the medical image acquiring unit, wherein, in the second display method, a plurality of recognition results which includes the recognition result is displayed in a list format, each recognition result of the plurality of recognition results includes a thumbnail image and a corresponding lesion-information label.

17. The medical image processing apparatus according to claim 1, wherein the plurality of the recognition results is displayed side by side on the display in the second display method.

* * * * *